(12) United States Patent
Comben

(10) Patent No.: US 6,497,705 B2
(45) Date of Patent: Dec. 24, 2002

(54) METHOD AND APPARATUS FOR CREATING A VIRTUAL ELECTRODE USED FOR THE ABLATION OF TISSUE

(75) Inventor: Richard H. Comben, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/903,274

(22) Filed: Jul. 11, 2001

(65) Prior Publication Data

US 2002/0019628 A1 Feb. 14, 2002

Related U.S. Application Data

(63) Continuation of application No. 09/347,380, filed on Jul. 6, 1999, now Pat. No. 6,315,777.
(60) Provisional application No. 60/091,948, filed on Jul. 7, 1998.

(51) Int. Cl.[7] ............................................. A61B 18/18
(52) U.S. Cl. ........................... 606/41; 606/49; 307/101
(58) Field of Search ........................... 606/34, 39, 40, 606/41–45, 49–50; 607/98–105, 115, 116, 122

(56) References Cited

U.S. PATENT DOCUMENTS

| | | | | |
|---|---|---|---|---|
| 5,785,706 A | * | 7/1998 | Bednarek | 600/372 |
| 5,897,553 A | * | 4/1999 | Muller et al. | 606/41 |
| 6,328,736 B1 | * | 12/2001 | Muller et al. | 604/35 |

* cited by examiner

*Primary Examiner*—Roy D. Gibson
(74) *Attorney, Agent, or Firm*—Daniel W. Latham, Esq.; Timothy A. Czaja, Esq.

(57) ABSTRACT

A method and apparatus for creating a virtual electrode to ablate bodily tissue. The surgical apparatus includes an inner tube and an outer tube. The inner tube defines a proximal portion and a distal portion. The distal portion forms an orifice for distributing a conductive solution from the inner tube and further forms an electrode. The outer tube coaxially receives the inner tube such that the outer tube is slidable relative to the inner tube. With this configuration, the outer tube selectively blocks flow of conductive solution from the orifice. During use, conductive solution distributed from the orifice is subjected to a current from the electrode, thereby creating a virtual electrode.

20 Claims, 5 Drawing Sheets

METHOD AND APPARATUS FOR CREATING A VIRTUAL ELECTRODE USED FOR THE ABLATION OF TISSUE

CROSS REFERENCE TO RELATED APPLICATION

This application is a continuation of U.S. application Ser. No. 09/347,380, filed on Jul. 6, 1999 now U.S. Pat. No. 6,315,777 and entitled "Method and Apparatus for Creating a Virtual Electrode Used for the Ablation of Tissue" that claims the benefit of U.S. Provisional Application No. 60/091,948, filed on Jul. 7, 1998.

FIELD OF THE INVENTION

The present invention relates generally to an apparatus for creating a virtual electrode. More particularly, the present invention relates to an apparatus for the creation of a virtual electrode that is useful for the ablation of soft tissue and neoplasms.

BACKGROUND OF THE PRESENT INVENTION

The utilization of an electric current to produce an ameliorative effect on a bodily tissue has a long history, reportedly extending back to the ancient Greeks. The effects on bodily tissue from an applied electric current, and thus the dividing line between harmful and curative effects, will vary depending upon the voltage levels, current levels, the length of time the current is applied, and the tissue involved. One such effect resulting from the passage of an electric current through tissue is heat generation.

Body tissue, like all non-superconducting materials, conducts current with some degree of resistance. This resistance creates localized heating of the tissue through which the current is being conducted. The amount of heat generated will vary with the power P deposited in the tissue, which is a function of the product of the square of the current I and the resistance R of the tissue to the passage of the current through it ($P=I^2R$).

As current is applied to tissue, then, heat is generated due to the inherent resistance of the tissue. Deleterious effects in the cells making up the tissue begin to occur at about 42° Celsius. As the temperature of the tissue increases because of the heat generated by the tissue's resistance, the tissue will undergo profound changes and eventually, as the temperature becomes high enough, that is, generally greater than 45° C., the cells will die. The zone of cell death is known as a lesion and the procedure followed to create the lesion is commonly called an ablation. As the temperature increases beyond cell death temperature, complete disintegration of the cell walls and cells caused by boiling off of the tissue's water can occur. Cell death temperatures can vary somewhat with the type of tissue to which the power is being applied, but generally will begin to occur within the range of 45° to 60° C., though actual cell death of certain tissue cells may occur at a higher temperature.

In recent times, electric current has found advantageous use in surgery, with the development of a variety of surgical instruments for cutting tissue or for coagulating blood. Still more recently, the use of alternating electric current to ablate, that is, kill, various tissues has been explored. Typically, current having a frequency from about 3 kilohertz to about 300 gigahertz, which is generally known as radiofrequency or radiofrequency (RF) current, is used for this procedure. Destruction, that is, killing, of tissue using an RF current is commonly known as radiofrequency ablation. Often radiofrequency ablation is performed as a minimally invasive procedure and is thus known as radiofrequency catheter ablation because the procedure is performed through and with the use of a catheter. By way of example, radiofrequency catheter ablation has been used to ablate cardiac tissue responsible for irregular heartbeats or arrhythmias.

The prior art applications of current to tissue have typically involved applying the current using a "dry" electrode. That is, a metal electrode is applied to the tissue desired to be affected and a generated electric current is passed through the electrode to the tissue. A commonly known example of an instrument having such an operating characteristic is an electrosurgical instrument known as a "bovie" knife. This instrument includes a cutting/coagulating blade electrically attached to a current generator. The blade is applied to the tissue of a patient and the current passes through the blade into the tissue and through the patient's body to a metal base electrode or ground plate usually placed underneath and in electrical contact with the patient. The base electrode is in turn electrically connected to the current generator so as to provide a complete circuit.

As the current from the bovie knife passes from the blade into the tissue, the resistance provided by the tissue creates heat. In the cutting mode, a sufficient application of power through the bovie knife to the tissue causes the fluid within the cell to turn to steam, creating a sufficient overpressure so as to burst the cell walls. The cells then dry up, desiccate, and carbonize, resulting in localized shrinking and an opening in the tissue. Alternatively, the bovie knife can be applied to bleeding vessels to heat and coagulate the blood flowing therefrom and thus stop the bleeding.

As previously noted, another use for electrical instruments in the treatment of the body is in the ablation of tissue. To expand further on the brief description given earlier of the ablation of cardiac tissue, it has long been known that a certain kind of heart tissue known as sino-atrial and atrio-ventricular nodes spontaneously generate an electrical signal that is propagated throughout the heart along conductive pathways to cause it to beat. Occasionally, certain heart tissue will "misfire", causing the heart to beat irregularly. If the errant electrical pathways can be determined, the tissue pathways can be ablated and the irregular heartbeat remedied. In such a procedure, an electrode is placed via a catheter into contact with the tissue and then current is applied to the tissue via the electrode from a generator of RF current. The applied current will cause the tissue in contact with the electrode to heat. Power will continue to be applied until the tissue reaches a temperature where the heart tissue dies, thereby destroying the errant electrical pathway and the cause of the irregular heartbeat.

Another procedure using RF ablation is transurethral needle ablation, or TUNA, which is used to create a lesion in the prostate gland for the treatment of benign prostatic hypertrophy (BPH) or the enlargement of the prostate gland. In a TUNA procedure, a needle having an exposed conductive tip is inserted into the prostate gland and current is applied to the prostate gland via the needle. As noted previously, the tissue of the prostate gland heats locally surrounding the needle tip as the current passes from the needle to the base electrode. A lesion is created as the tissue heats and the destroyed cells may be reabsorbed by the body, infiltrated with scar tissue, or just become non-functional.

While there are advantages and uses for such "dry" electrode instruments, there are also several notable disadvantages. One of these disadvantages is that during a procedure, coagulum—dried blood cells and tissue cells—will form on the electrode engaging the tissue. Coagulum acts as an insulator and effectively functions to prevent current transfer from the blade to the tissue. This coagulum "insulation" can be overcome with more voltage so as to keep the current flowing, but only at the risk of arcing and injuring the patient. Thus, during surgery when the tissue is cut with an electrosurgical scalpel, a build-up of coagulated blood and desiccated tissue will occur on the blade, requiring the blade to be cleaned before further use. Typically, cleaning an electrode/scalpel used in this manner will involve simply scraping the dried tissue from the electrode/scalpel by rubbing the scalpel across an abrasive pad to remove the coagulum. This is a tedious procedure for the surgeon and the operating staff since it requires the "real" work of the surgery to be discontinued while the cleaning operation occurs. This procedure can be avoided with the use of specially coated blades that resist the build up of coagulum. Such specialty blades are costly, however.

A second disadvantage of the dry electrode approach is that the electrical heating of the tissue creates smoke that is now known to include cancer-causing agents. Thus, preferred uses of such equipment will include appropriate ventilation systems, which can themselves become quite elaborate and quite expensive.

A further, and perhaps the most significant, disadvantage of dry electrode electrosurgical tools is revealed during cardiac ablation procedures. During such a procedure, an electrode that is otherwise insulated but having an exposed, current carrying tip is inserted into the heart chamber and brought into contact with the inner or endocardial side of the heart wall where the ablation is to occur. The current is initiated and passes from the current generator to the needle tip electrode and from there into the tissue so that a lesion is created. Typically, however, the lesion created by a single insertion is insufficient to cure the irregular heartbeat because the lesion created is of an insufficient size to destroy the errant electrical pathway. Thus, multiple needle insertions and multiple current applications are almost always required to ablate the errant cardiac pathway, prolonging the surgery and thus increasing the potential risk to the patient.

This foregoing problem is also present in TUNA procedures, which similarly require multiple insertions of the needle electrode into the prostate gland. Failing to do so will result in the failure to create a lesion of sufficient size otherwise required for beneficial results. As with radiofrequency catheter ablation of cardiac tissue, then, the ability to create a lesion of the necessary size to alleviate BPH symptoms is limited and thus requires multiple insertions of the electrode into the prostate.

A typical lesion created with a dry electrode using RF current and a single insertion will normally not exceed one centimeter in diameter. This small size—often too small to be of much or any therapeutic benefit—stems from the fact that the tissue surrounding the needle electrode tends to desiccate as the temperature of the tissue increases, leading to the creation of a high resistance to the further passage of current from the needle electrode into the tissue, all as previously noted with regard to the formation of coagulum on an electrosurgical scalpel. This high resistance—more properly termed impedance since typically an alternating current is being used—between the needle electrode and the base electrode is commonly measured by the RF current generator. When the measured impedance reaches a predetermined level, the generator will discontinue current generation. Discontinuance of the ablation procedure under these circumstances is necessary to avoid injury to the patient.

Thus, a typical procedure with a dry electrode may involve placing the needle electrode at a first desired location; energizing the electrode to ablate the tissue; continue applying current until the generator measures a high impedance and shuts down; moving the needle to a new location closely adjacent to the first location; and applying current again to the tissue through the needle electrode. This cycle of electrode placement, electrode energization, generator shut down, electrode re-emplacement, and electrode re-energization, will be continued until a lesion of the desired size has been created. As noted, this increases the length of the procedure for the patient. Additionally, multiple insertions increases the risk of at least one of the placements being in the wrong location and, consequently, the risk that healthy tissue may be undesirably affected while diseased tissue may be left untreated. The traditional RF ablation procedure of using a dry ablation therefore includes several patient risk factors that both patient and physician would prefer to reduce or eliminate.

The therapeutic advantages of RF current could be increased if a larger lesion could be created safely with a single positioning of the current-supplying electrode. A single positioning would allow the procedure to be carried out more expeditiously and more efficiently, reducing the time involved in the procedure. Larger lesions can be created in at least two ways. First, simply continuing to apply current to the patient with sufficiently increasing voltage to overcome the impedance rises will create a larger lesion, though almost always with undesirable results to the patient. Second, a larger lesion can be created if the current density, that is, the applied electrical energy, could be spread more efficiently throughout a larger volume of tissue. Spreading the current density over a larger tissue volume would correspondingly cause a larger volume of tissue to heat in the first instance. That is, by spreading the applied power throughout a larger tissue volume, the tissue would heat more uniformly over a larger volume, which would help to reduce the likelihood of generator shutdown due to high impedance conditions. The applied power, then, will cause the larger volume of tissue to be ablated safely, efficiently, and quickly.

Research conducted under the auspices of the assignee of the present invention has focused on spreading the current density throughout a larger tissue volume through the creation, maintenance, and control of a—virtual electrode—within or adjacent to the tissue to be ablated. A virtual electrode can be created by the introduction of a conductive fluid, such as isotonic or hypertonic saline, into or onto the tissue to be ablated. The conductive fluid will facilitate the spread of the current density substantially equally throughout the extent of the flow of the conductive fluid, thus creating an electrode—a virtual electrode—substantially equal in extent to the size of the delivered conductive fluid. RF current can then be passed through the virtual electrode into the tissue.

A virtual electrode can be substantially larger in volume than the needle tip electrode typically used in RF interstitial ablation procedures and thus can create a larger lesion than can a dry, needle tip electrode. That is, the virtual electrode spreads or conducts the RF current density outward from the RF current source—such as a current carrying needle, forceps or other current delivery device—into or onto a larger volume of tissue than is possible with instruments that rely on the use of a dry electrode. Stated otherwise, the creation of the virtual electrode enables the current to flow with reduced resistance or impedance throughout a larger volume of tissue, thus spreading the resistive heating created by the current flow through a larger volume of tissue and thereby creating a larger lesion than could otherwise be created with a dry electrode.

While the efficacy of RF current ablation techniques using a virtual electrode has been demonstrated in several studies, the currently available instruments useful in such procedures lags behind the research into and development of hoped-for useful treatment modalities for the ablation of soft tissue and malignancies.

It would be desirable to have an apparatus capable of creating a virtual electrode for the controlled application of tissue ablating RF electric current to a tissue of interest so as to produce a lesion of desired size and configuration.

SUMMARY OF THE INVENTION

One aspect of the present invention provides a surgical apparatus for creating a virtual electrode for ablating bodily tissue. The surgical apparatus includes an inner tube and an outer tube. The inner tube defines a proximal portion and a distal portion. The distal portion forms an orifice for distributing a conductive solution from the inner tube and further forms an electrode. The outer tube coaxially receives the inner tube. More particularly, the outer tube is slidable relative to the inner tube such that the outer tube selectively blocks the orifice.

Another aspect of the present invention relates to a surgical system for creating a virtual electrode for ablating bodily tissue. The surgical system includes a fluid source, a current source and a surgical instrument. The fluid source maintains a supply of a conductive solution. The current source is configured to generate an electrical current. The surgical instrument includes an inner tube, an outer tube and an electrode. The inner tube is fluidly connected to the fluid source and defines a proximal portion and a distal portion, with the distal portion forming an orifice for releasing the conductive solution from the inner tube. The outer tube is coaxially disposed over the inner tube such that the outer tube is slidable relative to the inner tube to selectively expose the orifice. Finally, the electrode is associated with the distal portion and is electrically connected to the current source.

Another aspect of the present invention relates to a method of forming a virtual electrode for ablating bodily tissue. The method includes providing a surgical instrument including an inner tube slidably received within an outer tube. The inner tube defines a proximal portion and a distal portion, the distal portion forming an orifice for distributing a conductive solution from the inner tube and further forming an electrode. The distal portion is delivered to a target site. The outer tube is positioned relative to the inner tube such that the orifice is exposed. Conductive solution is distributed from the inner tube via the orifice. The outer tube is repositioned relative to the inner tube such that the orifice is blocked. Finally, a current is applied to the distributed conductive solution via the electrode to create a virtual electrode.

DETAILED DESCRIPTION OF THE PREFERRED EMBODIMENTS

Figure 1:
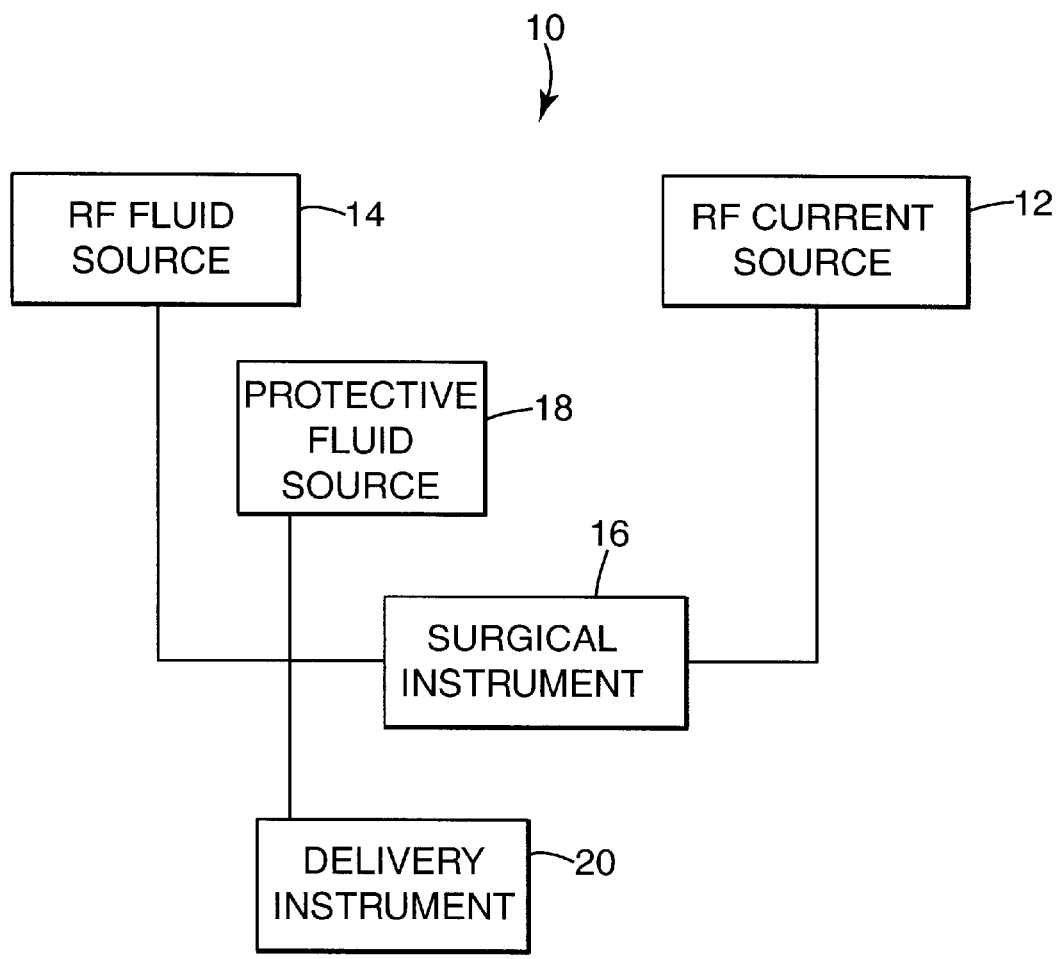
FIG. 1 is a block diagram of a virtual electrode ablation system in accordance with the present invention.

FIG. 1 illustrates in block form a system 10 for RF ablation useful with the present invention. The system 10 includes a source of radiofrequency alternating electric current 12, a source of RF ablating fluid 14, including but not limited to saline and other conductive solutions, and a surgical instrument 16 for delivering RF current and ablation fluid to a tissue site (not shown) for ablation purposes. In one preferred embodiment, the surgical instrument 16 is connected to the current source 12 and the fluid source 14. It will be understood that the current source 12 and the fluid source 14 may be combined into a single operational structure controlled by an appropriate microprocessor for a controlled delivery of ablating fluid and a controlled application of RF current, both based upon measured parameters such as but not limited to, flow rate, tissue temperature at the ablation site and at areas surrounding the ablation site, impedance, the rate of change of the impedance, the detection of arcing between the surgical instrument and the tissue, the time period during which the ablation procedure has been operating, and additional factors as desired.

While the surgical instrument 16 is shown as being connected to both the current source 12 and the fluid source 14, the present system is not so limited but could include separate needles or other instruments useful in RF liquid ablation procedures, that is, for example, a single straight or coiled needle having an exposed end and a fluid flow path there through could be used to deliver both fluid and current to the target tissue for ablation purposes. Alternatively, a separate needle could be used to deliver the current and a separate needle or needles could be used to deliver fluid to the target tissue. In addition, the application of the present system is not limited to the use of straight needles or helical needles as surgical instruments but could find use with any type of instrument wherein a conductive solution is delivered to a tissue and an RF current is applied to the tissue through the conductive fluid. Such instruments thus would include straight needles, helical needles, forceps, roller balls, instruments for the treatment of vascular disorders, and any other instrument.

In one preferred embodiment, the system 10 further includes a second fluid source 18 for delivery of tissue protecting fluid via a delivery instrument 20, to a tissue whose ablation is not desired.

Figure 2:
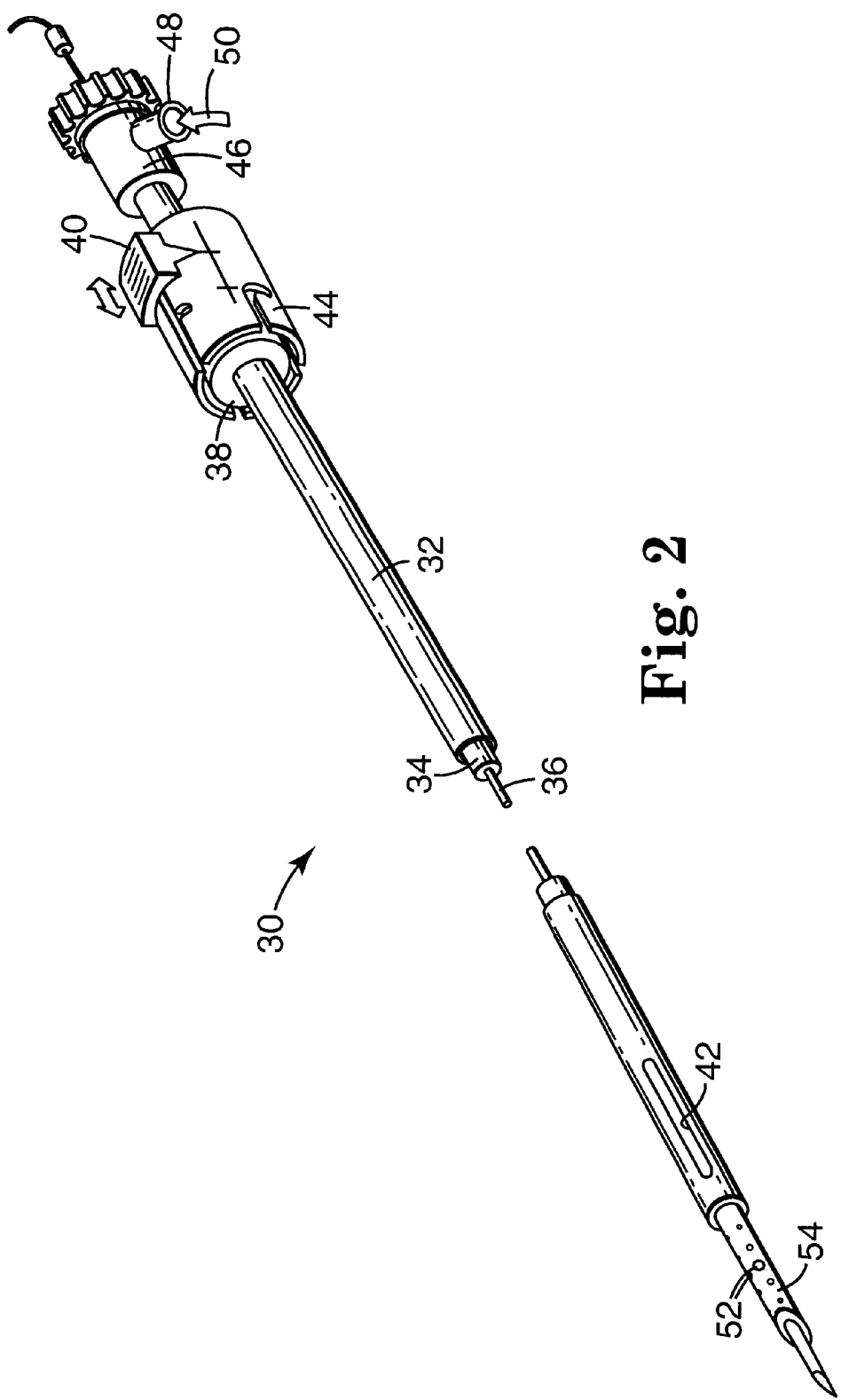
FIG. 2 is a perspective view of a surgical apparatus, with portions cut away, in accordance with the present invention.

The surgical instrument 16 may assume a wide variety of forms. One preferred embodiment of a surgical apparatus 30 useful in an RF ablation procedure is shown in FIG. 2. The apparatus 30 includes an outer thin walled tube 32, an inner thinner walled tube 34, and may, if desired, include an inner stylet or probe 36. Tubes 32 and 34 and stylet 36 are substantially coaxially mounted relative to each other and are movable in the proximal-distal direction relative to each other.

The outer tube 32 preferably includes a collar 38 with a control knob 40 attached at a proximal end thereof. The outer tube 32 further preferably includes at least one slot or aperture 42 located at a distal end thereof. If desired, multiple apertures 42 may be disposed in any desired manner about the circumference of the distal end of the outer tube 32. The aperture 42 may take on multiple configurations. In the embodiment shown in FIG. 2, the aperture 42 has an elongated oval or elliptical configuration.

In one preferred embodiment, the inner tube 34 is configured as a needle electrode. The inner tube 34, which is slidably received within the outer tube 32, preferably includes a shutter index element 44 attached adjacent a proximal end thereof. The shutter index element 44 will be discussed in further detail below. Attached to a proximal end of the inner tube 34 is a hemostasis valve 46 having a port 48 through which RF ablating fluid, such as but not limited to saline and other conductive solutions, may be supplied from the fluid source 14 (FIG. 1) as indicated by arrow 50. A distal end of the inner tube 34 includes a plurality of orifices or apertures 52 of varying sizes and shapes as desired. As shown in FIG. 2, there are preferably four sets of the apertures 52 equally spaced about a circumference of the distal end of the inner tube 34. In one preferred embodiment, each set includes five apertures increasing in size toward a center of the individual set. Thus, during use, as fluid flows through the apertures 52, more of the fluid will flow through the center aperture than will flow through the other apertures. As a result, the bolus of the fluid forming at a particular target site may take on a roughly elliptical shape, making allowances for the tissue at the target site and the vasculature that may be implicated by any particular placement.

The inner tube 34 includes at its most distal end an exposed electrode 54 through which RF current can be applied to the tissue. Thus, the inner tube 34 may be metallic or otherwise conductive and insulated along its length except for the exposed electrode 54. The electrode 54 is preferably electrically connected to the current source 12 (FIG. 1).

Figure 3:
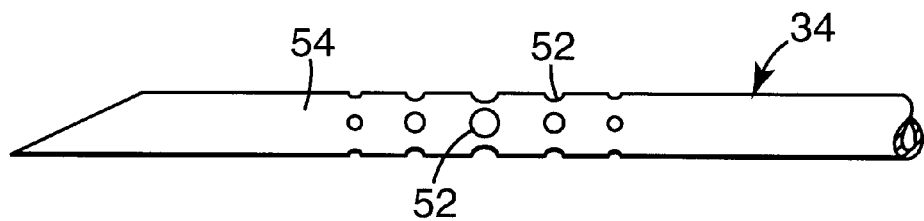
FIG. 3 is an enlarged, side view of a distal portion of the surgical apparatus of FIG. 2.

FIG. 3 illustrates a plan view of the distal end of the inner tube or needle electrode 34. It will be understood that the needle electrode 34 will be insulated except at the distal end to prevent electrical current from flowing into the tissue (not shown) at any location except from the distal end thereof.

Returning to FIG. 2, the probe 36 may take the form of an inner stylet, preferably having a thermocouple (not shown) disposed at the distal end thereof. Because the probe 36 is movable relative to the electrode 54, the thermocouple may be placed at a desired location away from the electrode to monitor tissue temperature.

Figure 4A:
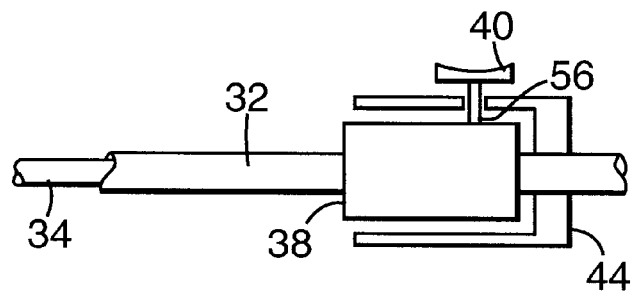
FIGS. 4A and 4B are schematic views of a portion of the surgical apparatus of FIG. 2.
Figure 4B:
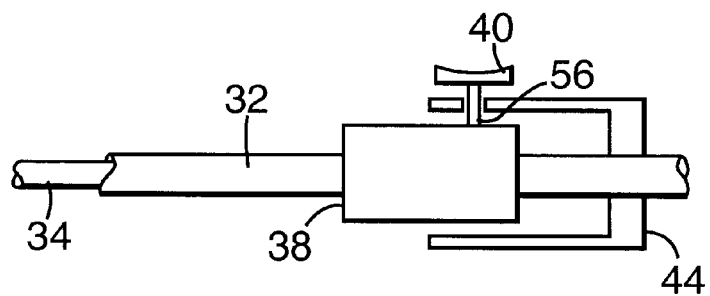
Figure 4C:
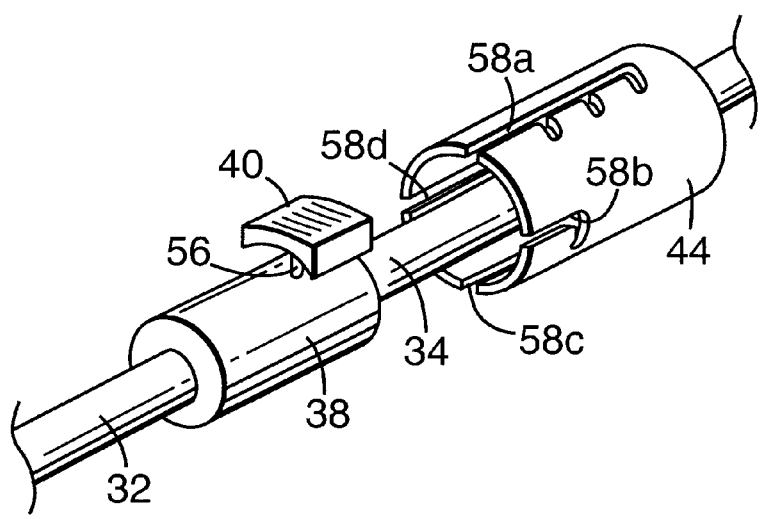
FIG. 4C is an exploded, perspective view of a portion of the surgical apparatus of FIG. 2.

FIGS. 4A–4C illustrate in greater detail the connections between the control knob 40 and the outer tube 32 on the one hand, and the shutter index element 44 and the inner tube 34 on the other. The control knob 40 is preferably connected to the collar 38 of the outer tube 32 by a support 56. The outer tube 32 and the control knob 40 are rotatable and axially movable relative to the inner tube 34 and the shutter index element 44. Thus, the control knob 40 can be selectively moved into and out of engagement with a portion of the shutter index element 44. For example, the control knob 40 may be rotated from a first engagement position (FIG. 4A), and then moved axially to a second engagement position (FIG. 4B). The outer tube 32 is maneuvered in conjunction with the control knob 40, and thus moves relative to the inner tube 34 with movement of the control knob 40. For example, as best shown in FIG. 4C, the shutter index element 44 is preferably configured to form axial slots 58a–58d sized to receive the support 56. Each of the axial slots 58a–58d is connected to at least one circumferential slot, similarly sized to receive and selectively maintain the support 56. For example, the axial slot 58a is shown as being connected to three circumferential slots 60, whereas the axial slot 58b is connected to one circumferential slot 62. Any other number of circumferential slots is equally acceptable and dictates a desired position(s) of the outer tube 32 relative to the inner tube 34, as described in greater detail below.

Translation of the control knob 40/outer tube 32 relative to the shutter index element 44/inner tube 34 and the effect on fluid flow is shown in greater detail in FIGS. 5–8. In each of FIGS. 5–8, the control knob 40 (FIG. 4A) has not been shown for purposes of clarity. Instead, only the support 56, which extends from the control knob 40 to the collar 38 (FIG. 4A), has been depicted. Further, the shutter index element 44 is shown as including the axial slot 58a connected to four circumferential slots 64a–64d. As previously described, the support 56 can be maneuvered along the axial slot 58a into selective engagement with each of the circumferential slots 64a–64d, thereby locating the support 56 within any one of the circumferential slots 64a–64d and resulting in a defined relationship of the outer tube 32 relative to the inner tube 34. To assist a user in positioning the support 56, the shutter index element 44 may further include indicia 66a–66d associated with the circumferential slots 64a–64d, respectively. The indicia 66a–66d may assume a wide variety of forms for providing a user with an indication of outer tube 32/inner tube 34 positioning. For example, the indicia 66a may be a filled circle ("Δ") representing that all of the orifices 52 of the inner tube 34 are open; the indicia 66b may be a half filled circle ("X") representing the orifices 52 being partially open; the indicia 66c may be an open circle ("o") representing all of the orifices 52 being closed; and the indicia 66d may be a dash ("—") representing the slot 42 of the outer tube 32 being open or aligned with the orifices 52.

Figure 5:
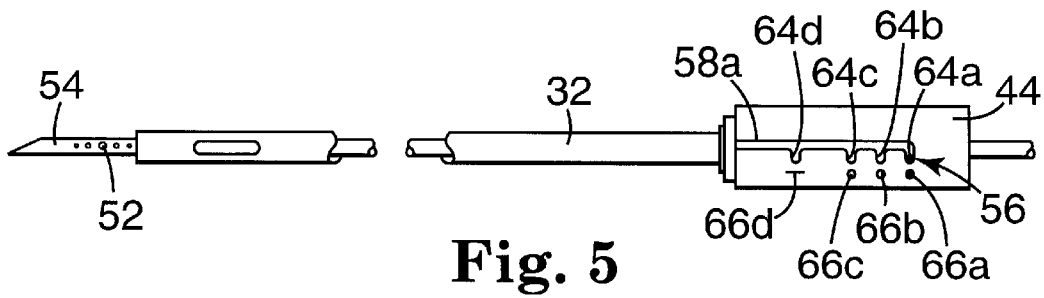
FIGS. 5–8 are side views of a surgical apparatus in accordance with the present invention, depicting various positions of an outer tube relative to an inner tube.

FIG. 5 illustrates the situation where the control knob 40 (FIG. 4A) has been moved to a position where the orifices 52 are fully opened and allow RF fluid to flow freely therefrom. That is to say, the support 56 is positioned within the circumferential slot 64a. At this location, a distal end of the outer tube 32 is proximal the orifices 52 and the electrode 54. Fluid from the fluid source 14 (FIG. 1) is thereby allowed to flow from the orifices 52.

Figure 6:
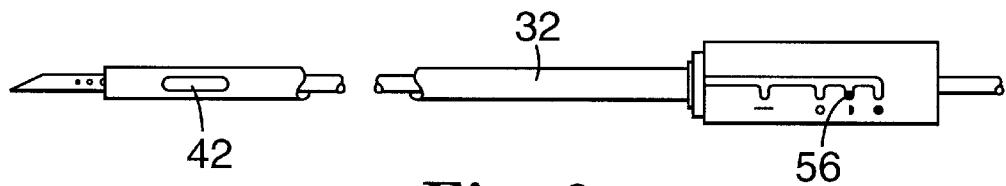

FIG. 6 illustrates the partial blocking of the orifices 52. In this instance, relative to FIG. 5, the control knob 40 (FIG. 4A) has been rotated relative to the shutter index element 42 and moved distally along the axial slot 58a so as to move the outer tube 32 distally relative to the inner tube 34. The control knob 40 has then been rotated radially to lodge the support 56 in the circumferential slot 64b. Movement of the outer tube 32 in this manner (e.g., distally) causes the outer tube 32 to partially block at least some of the orifices 52 and thus restrict or stop RF fluid flow therefrom, as identified by the indicia 66b.

Figure 7:
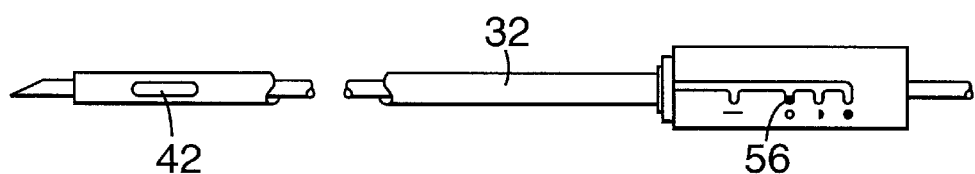
Figure 8:
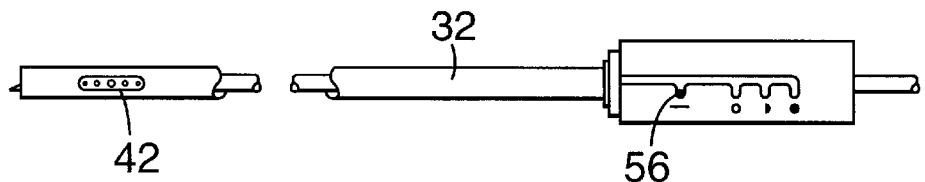

FIG. 7 illustrates the complete blocking of RF fluid flow from all of the apertures 52. More particularly, the support 56 has been moved into the circumferential slot 66c, resulting in a distal end of the outer tube 32 being distal the orifices 52. In FIG. 8, the slot 42 at the distal end of outer tube 32 has been moved such that fluid flows only from the orifices 52 and then through the slot 42, thus providing in essence a single aperture along a longitudinal length of the outer tube 32 rather than discrete multiple apertures. The indicia 66d provides visual notice of this relationship to the user.

The present invention allows an operator to block the distribution of the RF fluid from the apparatus 30 in a selective manner. This allows the operator to control the volume of the fluid flow and the shape of the bolus or virtual electrode produced in the tissue with some degree of latitude as allowed by the tissue structure in which the apparatus is placed.

Although the present invention has been described with reference to preferred embodiments, workers skilled in the art will recognize that changes may be made in form and detail without departing from the spirit and scope of the invention.

What is claimed is:

1. A surgical apparatus for creating a virtual electrode to ablate bodily tissue, the surgical apparatus comprising:
    an inner tube defining a proximal portion and a distal portion, the distal portion forming an orifice for distributing a conductive fluid from the inner tube and further forming an electrode;
    an outer tube coaxially disposed about the inner tube, wherein the outer tube is slidable relative to the inner tube such that the outer tube selectively covers the orifice;
    a shutter index element connected to the proximal portion of the inner tube, the shutter index element configured to control flow from the orifice by dictating a position of the outer tube relative to the inner tube.

2. The surgical apparatus of claim 1, wherein the shutter index element indicates a position of the outer tube relative to the inner tube.

3. The surgical apparatus of claim 1, wherein the outer tube defines a proximal end and a distal end, the surgical apparatus further comprising:
    a support connected to the proximal end of the outer tube, the support being sized to selectively engage a portion of the shutter index element.

4. The surgical apparatus of claim 3, wherein the shutter index element forms an axial slot sized to guide the support and a circumferential slot sized to selectively maintain the support, the circumferential slot being located to dictate a desired position of the outer tube relative to the inner tube.

5. The surgical apparatus of claim 4, wherein the shutter index element forms a plurality of spaced circumferential slots including first and second circumferential slots, the first and second circumferential slots being located such that when the support is received within the first circumferential slot, the outer tube covers an entirety of the orifice and when the support is received within the second circumferential slot, the outer tube does not cover an entirety of the orifice.

6. The surgical apparatus of claim 4, wherein the distal portion of the inner tube forms a plurality of orifices each configured to distribute a conductive fluid from the inner tube, and further wherein the shutter index element is configured to dictate a first position in which the outer tube covers all of the plurality of orifices and a second position in which the outer tube covers none of the plurality of orifices.

7. The surgical apparatus of claim 6, wherein the shutter index element is configured to visually indicate maximum fluid distribution in the first position and minimum fluid distribution in the second position.

8. The surgical apparatus of claim 6, wherein the shutter index element is configured to dictate a third position in which only some of the plurality of orifices are covered.

9. The surgical apparatus of claim 6, wherein the outer tube defines a proximal end and an a distal end, and forms a slot proximal the distal end, and further wherein the shutter index element is configured to provide a fourth position in which the slot is aligned with at least one of the plurality of orifices.

10. The surgical apparatus of claim 9, wherein the slot is aligned with all of plurality of orifices in the fourth position.

11. A surgical system for creating a virtual electrode to ablate bodily tissue, the surgical system comprising:
    a fluid source maintaining a supply of conductive solution;
    a current source configured to selectively supply an electrical current; and
    a surgical instrument including:
        an inner tube fluidity connected to the fluid source, the inner tube defining a proximal portion and a distal portion, wherein the distal portion forms an orifice for releasing the conductive solution from the inner tube,
        an outer tube collaxialy disposed about the inner tube, wherein the outer tube is slidable relative to the inner tube such that the outer tube selectively covers the orifice,
        an electrode associated with the distal portion of the inner tube, the electrode being electrically connected to the current source to energize conductive solution released from the inner tube,
        a shutter index element connected to the proximal portion of the inner tube, the shutter index element configured to control flow from the orifice by dictating a position of the outer tube relative to the inner tube.

12. The surgical system of claim 11, wherein the distal portion of the inner tube forms a plurality of orifices each configured to distribute the conductive fluid from the inner tube, and further wherein the shutter index element is configured to dictate a first position in which the outer tube covers all of the plurality of orifices and a second position in which the outer tube covers none of the plurality of orifices.

13. The surgical system of claim 12, wherein the shutter index element is configured to visually indicate maximum fluid distribution in the first position and minimum fluid distribution in the second position.

14. The surgical system of claim 12, wherein the shutter index element is configured to dictate a third position in which only some of the plurality of orifices are covered.

15. The surgical system of claim 12, wherein the outer tube defines a proximal end and a distal end and forms a slot proximal the distal end, and further wherein the shutter index element is configured to provide a fourth position in which the slot is aligned with at least one of the plurality of orifices.

16. The surgical system of claim 15, wherein the slot is aligned with all of the plurality of orifices in the fourth position.

17. A method for ablating bodily tissue of a patient, the method comprising:
    providing a surgical instrument including an inner tube, an outer tube and a shutter index element, the inner tube forming an orifice and an electrode at a distal portion thereof and being slidably received within the outer tube such that the outer tube selectively blocks the orifice, a position of the outer tube relative to the orifice being dictated by the shutter index element;
    determining a desired distribution pattern of conductive solution;
    adjusting the shutter index element to position the outer tube relative to the orifice based upon the desired distribution pattern;
    positioning the distal portion of the inner tube adjacent the bodily tissue to be ablated;

distributing a conductive solution at the target site via the orifice;

applying a current to the distributed conductive solution via the electrode to ablate the bodily tissue.

18. The method of claim 17, wherein the shutter index element includes a plurality of slots each configured to receive a support connected to the outer tube and indicia associated with each of the slots, the indicia indicative of a distribution pattern, and further wherein interacting with the shutter index element includes positioning the support within a one of the plurality of slots having indicia corresponding with the desired distribution pattern.

19. The method of claim 17, wherein the inner tube forms a plurality of orifices, a method further comprising:

covering all the orifices formed at the distal portion of the inner tube with the outer tube.

20. The method of claim 17, wherein the inner tube forms a plurality of axially aligned orifices, and wherein a distal end of the outer tube forms a slot, and further wherein interacting with the shutter index element includes aligning the slot over the plurality of axially aligned orifices.

* * * * *